US005950621A

United States Patent [19]

Klockseth et al.

[11] Patent Number: 5,950,621

[45] Date of Patent: Sep. 14, 1999

[54] POWERED AIR-PURIFYING RESPIRATOR MANAGEMENT SYSTEM

[75] Inventors: Martinus Oliver Klockseth, Belrose; Bengt Yngve Roland Jervmo, Green Point; Goran Bertil Claes Berndtsson, Elanora Heights, all of Australia

[73] Assignee: Safety Equipment Sweden AB, Warriewood, Australia

[21] Appl. No.: 08/913,795

[22] PCT Filed: Mar. 22, 1996

[86] PCT No.: PCT/AU96/00164

§ 371 Date: Dec. 12, 1997

§ 102(e) Date: Dec. 12, 1997

[87] PCT Pub. No.: WO96/29116

PCT Pub. Date: Sep. 26, 1996

[30] Foreign Application Priority Data

Mar. 23, 1995 [AU] Australia .................................. PN1910

[51] Int. Cl.[6] .................................................... A61M 16/00

[52] U.S. Cl. ................................ 128/204.26; 128/201.25; 128/202.22; 128/205.23

[58] Field of Search ......................... 128/201.25, 202.22, 128/205.23, 205.25, 206.15, 204.26, 205.18, 205.22

[56] References Cited

U.S. PATENT DOCUMENTS

| | | | |
|---|---|---|---|
| 3,765,239 | 10/1973 | Olsson | 128/205.23 |
| 4,276,877 | 7/1981 | Gdula | 128/204.26 |
| 4,674,492 | 6/1987 | Niemeyer | 128/206.15 |
| 4,873,470 | 10/1989 | Freidank et al. | 128/202.22 |
| 4,899,740 | 2/1990 | Napolitano | 128/205.23 |
| 5,018,518 | 5/1991 | Hubner | 128/202.22 |
| 5,036,842 | 8/1991 | van der Smissen et al. | 128/201.25 |
| 5,253,640 | 10/1993 | Falb et al. | 128/205.18 |
| 5,297,544 | 3/1994 | May . | |
| 5,322,058 | 6/1994 | Pasternack | 128/204.26 |
| 5,413,097 | 5/1995 | Birenheide et al. | 128/202.22 |
| 5,577,496 | 11/1996 | Blackwood et al. | 128/201.25 |
| 5,666,949 | 9/1997 | Debe et al. | 128/202.22 |
| 5,715,812 | 2/1998 | Deighan et al. | 128/204.23 |

FOREIGN PATENT DOCUMENTS

| | | |
|---|---|---|
| 2503153 | 10/1975 | Germany . |
| 4002843 C1 | 4/1991 | Germany . |

*Primary Examiner*—Aaron J. Lewis
*Attorney, Agent, or Firm*—Townsend and Townsend and Crew LLP

[57] ABSTRACT

The present invention relates to a particular type of fan-forced positive pressure breathing apparatus, commonly known as Powered Air-Purifying Respirators (PAPRs). In particular the invention concerns monitoring the operation of such equipment. In a first aspect, the invention provides a powered air-purifying respirator which includes data collection means to enable the volume of air drawn through the filter to be determined. In another aspect, the invention comprises a management system for monitoring and analyzing operational data from at least one powered air-purifying respirator. The management system includes data collection means associated with each respirator to enable the volume of air drawn through that respirator's filter to be determined, and electronic data processing apparatus into which the data collected by the data collection means is uploaded for analysis. The data processing apparatus may be partly situated on-board each respirator in order to enable alarms to be given to the wearers at appropriate times. However, a remote computer system having data processing facilities will be able to store and subsequently display the data collected, as well as enabling more sophisticated analysis.

11 Claims, 1 Drawing Sheet

POWERED AIR-PURIFYING RESPIRATOR MANAGEMENT SYSTEM

FIELD OF THE INVENTION

The present invention relates to a particular type of fan-forced positive pressure breathing apparatus, commonly known as Powered Air-Purifying Respirators (PAPRs). In particular the invention concerns monitoring the operation of such equipment.

BACKGROUND ART

Non-powered air-purifying respirator equipment involves a breathing mask having a filtered air inlet. Air is drawn through the filter by means of the wearer's breathing action. A considerable problem with this type of respirator is how to determine when the filter is due to be replaced. A number of "end-of-service-life" indicators have been proposed over the years, but none have been widely adopted. The major difficulty is that the useful life of the filter is determined by several non-related factors, such as the proportion of contaminant in the atmosphere, the humidity and the effort required of the user. Present estimates of filter lifetime are based on a number of such factors, and it takes considerable experience to weigh them together.

In recent years positive air-pressure respirators have been introduced, and these employ a pump which draws ambient air in through a filter and supply it to the face mask. The pump comprises a motorized fan which draws air through the filter in proportion to the speed of revolution. In such simple motorized equipment the filter life, in a particular environment, is directly related to the operating time and in practice can be estimated with reasonable reliability. However, these respirators suffer from the problems that they do not necessarily provide sufficient air flow for periods of maximum inhalation, but are otherwise wasteful in filter usage by providing excess flow during exhalation cycles.

A new generation of powered air-purifying respirators (PAPRs) that has been developed by the applicant employs a breathing demand valve to overcome the deficiencies of the simple positive air-pressure respirators mentioned above. However, the inclusion of the demand valve has reintroduced the unpredictable variant of air consumption into the determination of filter life.

DISCLOSURE OF THE INVENTION

In a first aspect, the invention provides a powered air-purifying respirator comprising: a face-piece to cover at least the mouth or nose of a wearer; a pump unit to supply ambient air to the face-piece via an air passage; a decontaminating means to filter the ambient air supplied to the face-piece; and a demand valve associated with the face-piece and responsive to a wearer's demand for air to deliver supplied air to the wearer. The respirator further includes data collection means to enable the volume of air drawn through the decontaminating means to be determined. This equipment takes advantage of the fact that the powered respirator has on-board power available to drive the data collection means.

The phrase "decontaminating means" has been used generically to indicate any means which is able to decontaminate the air for the wearer. The decontaminating means has been described with reference to a "filter" when that word has been used in a broad functional sense. It should be appreciated that the word "filter" also has a jargon meaning in this field to refer to a device for the mechanical removal of particles from the air; a filter usually comprises a fine mesh that will let air pass but not particles. The phrase "decontaminating means" also includes within its scope:

absorbers which suck up contaminants, like a sponge;

adsorbers to the surface of which contaminants adhere, for example carbon based gas filters; and catalysts which transform a contaminant into a different material through a chemical reaction, for example "carbon monoxide filters".

The phrase "face-piece" has been used generically to indicate any apparatus which covers at least the mouth or nose of a wearer, and it includes a mask, hood or headpiece.

The data collection means may comprise a flow meter to measure the instantaneous flow of air within the respirator, and a clock. The flow meter and clock are operable to form an accumulating volume meter, enabling the total volume of air drawn through the decontaminating means to be determined. The flow meter can be situated anywhere in the air passage where a true flow value may be measured.

The actual determination of the volume of air drawn through the decontaminating means need not be conducted on-board the respirator, but if the determination is made on-board, then an alarm can conveniently be provided to the wearer when the decontaminating means nears the end of its useful life.

Whether the volume is determined on-board the respirator, or not, it will be advantageous to include a data port to enable either the raw data measured by the measuring means, or the volume data determined, to be uploaded to a remote computer system. The computer system may include a database containing information about many respirants and enable an administrator to closely observe their operation and performance. This may also enable the administrator to ensure the wearers are operating the respirators in a safe fashion.

An additional feature is to associate identification marks with each respirator, or with some or all components of each respirator, in order to permit logging of those identifications into the database. The identification marks will generally comprise unique indicia and may involve the use of techniques such as barcodes or magnetic coded strips.

Identity coding of each decontaminating means enables the performance characteristics of each type to be analyzed. The analysis may consider data such as the types and concentrations of contaminants, the humidity, the temperature, the periods of use, the flow resistance and the maximum air flow rate through the decontaminating means. From such analysis it is possible to predict the optimum life of a particular type of decontaminating means in any particular application or environment.

On-board power will usually be provided to the respirator by rechargeable batteries. Operational data, such as battery voltage, may also be measured on-board. An alarm signal may then be sent to the wearer in advance of discharge. More sophisticated systems may monitor the time since the last recharging and the operational time of each battery, using its identification, to predict battery failure in advance. An alarm could then be displayed at the time of collection of the respirator or at the time of return, to ensure recharging before use. Where a stack of batteries are used each individual cell may be monitored, which is useful as the performance of a battery is limited by the performance of the weaker cell in a stack.

Alarms to the wearer may be provided in the form of a displayed message, an audible tone, a warning light or combinations of these. The alarm may be issued as a simple signal or as a more complex sequence of warnings. Flashing lights, intensity modulations or color shift may be used to indicate different levels of seriousness of the alarm. Fail-safe operation of the alarm may also be included in the alarm scheme.

Air flow measurement may be made by an air flow restrictor such as an orifice plate or mesh and a pressure sensor adapted to measure the change in pressure across the restrictor. Alternatively, the air flow restrictor may comprise an air transfer hose, and the air flow may be measured by a pressure sensor adapted to measure the change in pressure between the pump unit and the face-piece. In another alternative, air flow measurement may be made by an ultrasound transmitter and receiver arranged to transmit and detect ultrasound travelling along a portion of the air transfer channel. The flow rate in this case is directly proportional to the time shift of the ultrasound travelling along the channel. This method has the advantage that it places no flow restriction in the air flow. In another alternative, flow measurement may be made by a heated thermistor placed in a stream of air: flow rate is then proportional to the cooling effect on the thermister.

Pressure may be measured by a silicon pressure transducer. In an alternative, pressure may be measured by a flexible membrane arranged to flex with changes in pressure, and an ultrasound detection system. The detection system may involve an ultrasound transmitter arranged to direct ultrasound at the membrane, an ultrasound receiver arranged to detect ultrasound reflected from the membrane and an analyzer capable of determining the change in transit time of the transmitted and received signals. The changes in transit time may be calibrated to provide an indication of air pressure. To compensate for changes in the transit time of the ultrasound caused by temperature variations, temperature probes may also be provided in both flow and pressure sensing systems.

In another aspect, the invention comprises a management system for monitoring and analyzing operational data from at least one powered air-purifying respirator of the type comprising: a face-piece to cover at least the mouth and nose of a wearer: a pump unit to supply ambient air to the face-piece via an air passage; a decontaminating means to filter the ambient air supplied to the face-piece: and a demand valve associated with the face-piece and responsive to a wearer's demand for air to deliver supplied air to the wearer. The management system includes data collection means associated with each respirator to enable the volume of air drawn through that respirator's decontaminating means to be determined, and electronic data processing apparatus into which the data collected by the data collection means is uploaded for analysis. The data processing apparatus may be partly situated on-board each respirator in order to enable alarms to be given to the wearers at appropriate times. However, a remote computer system having data processing facilities will be able to store the data in a database and subsequently display the data collected as well as enabling more sophisticated analysis.

The respirators, and some or all of their component parts, may be identified in order to enable the management system to log data about the operation of the various components. From the information the management system may provide other warnings, such as imminent battery failure, as well as performance analysis.

BRIEF DESCRIPTION OF THE DRAWINGS

An example of the invention will now be described with reference to the schematic arrangement of FIG. 1.

DESCRIPTION OF THE PREFERRED EMBODIMENT

Figure 1:
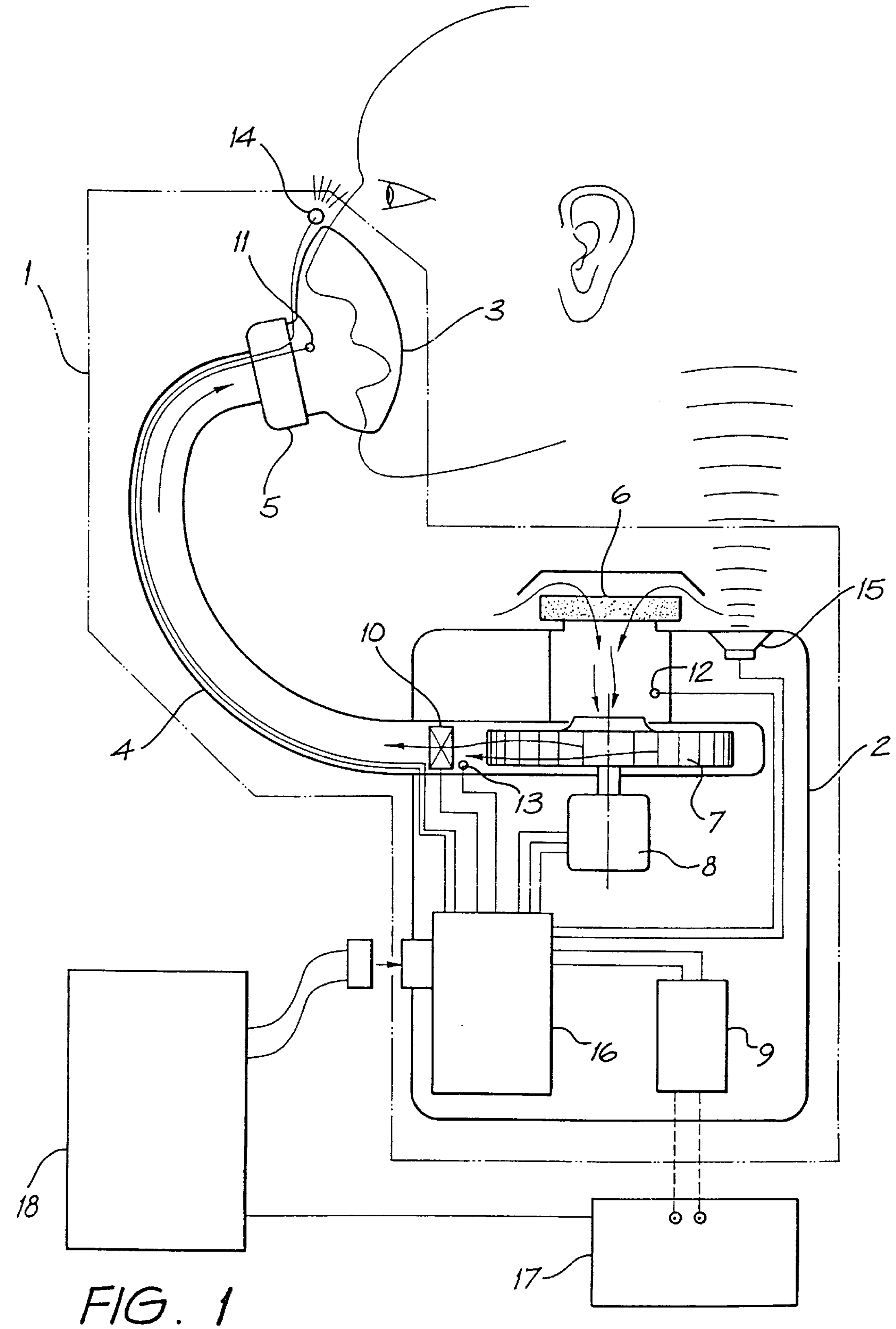

A powered air-purifying respirator is generally shown at 1. The respirator includes a pump unit 2, and a face-piece 3 comprising a mask which is adapted to cover the nose and mouth of a wearer, and is adjustable to fit snugly to the contours of the wearer's face. The pump unit 2 and mask 3 are interconnected by an air passage defined by flexible hose 4. A demand valve 5 is positioned at the point where the flexible hose 4 enters the mask 3. The demand valve 5 delivers air to the mask according to the wearer's instantaneous requirements from the pressurized supply in tube 4. A filter 6 is positioned at the air inlet of pump unit 2. In use ambient air is drawn through filter 6 at the air inlet and supplied to mask 3 through hose 4.

Inside pump unit 2 is a centrifugal fan 7 and an electronic motor 8 to drive the fan 7. A rechargeable battery 9 provides electrical power to the respirator. In addition to driving motor 8, battery 9 provides electrical power to a flow meter 10 positioned at or within flexible pipe 4, a pressure sensor 11 in mask 3, a second pressure sensor 12 positioned in the air inlet behind filter 6 and a third pressure sensor 13 located at the outlet of the fan. In addition battery 9 supplies electrical power to a warning light 14 in mask 3, and an audible buzzer 15 in pump unit 2.

The pump unit 2 also includes data collection electronics 16 which receives inputs from motor 8, battery 9, flow meter 10 and pressure sensors 11, 12 and 13. The collected data may be time stamped every time a record is logged. Data processing logic within the data collection module 16 responds to the inputs to provide warnings to the wearer. In particular, electronics 16 measures the instantaneous flow of filtered air through pipe 4, and this is combined with a measurement of the time during which the respirator has been in use to determine the volume of air that has passed through filter 6. This information can be used to provide an alarm when the filter nears or reaches the end of its working life. The alarm is visual by light 14 and audible by buzzer 15.

The electronics 16 also monitors the battery 9 voltage, and warns the user of impending battery failure by light 14 and buzzer 15. The battery can then be recharged by recharger 17.

Data logged by the electronics 16 is periodically uploaded to a database in a remote computer system 18 to enable storage and further analysis of the data logged. Uploading the data provides a mechanism for system management.

The remote computer system receives not only operational data from the flow meter and sensors, but also data concerning alarm events. A system administrator will enter the identity code of each component as each respirator is assembled. This information may be marked with a barcode label on each component. He will also enter the environmental information, such as the type of contaminant, the degree of contamination, the humidity and the temperature, each day or as regularly as required. This information allows not only monitoring of the operational history and performance of each component, but also provides a facility for predicting failure modes. Such prediction can be used to create service regimes and component replacement schedules. The administrator will ensure that the components are changed at the times required, and that the new component identities are entered.

Most importantly this information is used to calculate the precise time at which the filters require replacing. A suitable margin may be added and a signal sent to the system administrator or the wearer when a filter requires replacing.

Although the invention has been described with reference to a particular embodiment, it should be appreciated that it may be embodied in many other forms. For instance the face-mask is not essential and the invention may be applied to any other form of respirator. The components need not be barcoded, and any other convenient identification scheme may be adapted. Further, the management system may also provide other warnings such as motor and fan service intervals, and it may provide reminders to upload data. In another variant the demand valve 5 may be positioned at the pump unit, and the filter may be positioned at the outlet of the pump. It should also be appreciated that any suitable type of pump could replace the centrifugal pump illustrated.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A powered air-purifying respirator, comprising:

a face-piece to cover at least the mouth or nose of a wearer;

a pump unit to supply ambient air to the face-piece via an air passage;

decontaminating means for filtering the ambient air supplied to the face-piece;

a demand valve associated with the face-piece or pump unit and responsive to a wearer s demand for air to deliver supplied air to the wearer; and data collection means for enabling the volume of air passing through the decontaminating means to be determined.

2. A powered air-purifying respirator according to claim 1, including a data port to enable the data collected by the data collection means to be uploaded to a remote computer system.

3. A powered air-purifying respirator according to claim 1, wherein on-board power is provided to the respirator by rechargeable batteries, the battery voltage is measured on board, and an alarm signal is sent to the wearer in advance of discharge.

4. A combination of a management system for monitoring an analyzing operational data from at least one powered air-purifying respirator and at least one powered air-purifying respirator, each respirator comprising a face-piece to cover at least the mouth and nose of a wearer; a pump unit to supply ambient air to the face-piece via an air passage; decontaminating means for filtering ambient air supplied to the face-piece; and a demand valve associated with the face-piece or pump unit and responsive to a wearer's demand for air to deliver supplied air to the wearer;

wherein the management system includes data collection means associated with each respirator to enable the volume of air drawn through the decontaminating means of the respirator to be determined; and an electronic data processing apparatus into which the data collected by the data collection means is uploaded for analysis.

5. A combination according to claim 4, wherein the data processing apparatus is at least partly situated on-board each respirator in order to enable warnings to be given to the wearers at appropriate times.

6. A combination according to claim 5, wherein the management system includes a remote computer system which contains at least part of the data processing apparatus, the remote computer system being configured to log the identities of each respirator, or some or all of the component parts of each respirator.

7. A combination according to claim 6, wherein identification marks are associated with each respirator, or with some or each component of each respirator, and wherein the remote computer system is configured to log the identification marks into a database.

8. A powered air purifying respirator, comprising:

a face-piece to cover at least the mouth or nose of a wearer;

a pump to supply ambient air to the face-piece via an air passage;

decontaminating means for filtering the ambient air supplied to the face-piece;

a demand valve associated with the face-piece or pump and responsive to a wearer's demand for air to deliver supplied air to the wearer;

a flow meter to measure the instantaneous flow of air within the respirator; and a clock operable to produce data which, in conjunction with instantaneous flow data from the flow meter, enables the accumulated volume of air drawn through the decontaminating means to be determined.

9. A powered air-purifying respirator according to claim 8, wherein the flow meter is situated in the air passage coupled between the pump and the face-piece.

10. A powered air purifying respirator, comprising:

a face-piece to cover at least the mouth or nose of a wearer;

a pump to supply ambient air to the face-piece via an air passage;

decontaminating means for filtering the ambient air supplied to the face-piece;

a demand valve associated with the face-piece or pump and responsive to a wearer's demand for air to deliver supplied air to the wearer; and data collection means for enabling the volume of air passing through the decontaminating means to be determined on-board the respirator.

11. A powered air purifying respirator according to claim 10, wherein an alarm is provided to the wearer when the useful life of the decontaminating means nears the end.

* * * * *